(12) United States Patent
Muller et al.

(10) Patent No.: US 9,486,415 B2
(45) Date of Patent: Nov. 8, 2016

(54) STARCH FOILS AND/OR FILMS AND A METHOD AND USE OF A DEVICE FOR THE PRODUCTION THEREOF

(75) Inventors: Rolf Muller, Zurich (CH); Federico Innerebner, Zurich (CH)

(73) Assignee: InnoGEL AG, Hunenberg (CH)

( * ) Notice: Subject to any disclaimer, the term of this patent is extended or adjusted under 35 U.S.C. 154(b) by 1245 days.

(21) Appl. No.: 13/255,045

(22) PCT Filed: Mar. 3, 2010

(86) PCT No.: PCT/EP2010/052717
§ 371 (c)(1),
(2), (4) Date: Sep. 26, 2011

(87) PCT Pub. No.: WO2010/100206
PCT Pub. Date: Sep. 10, 2010

(65) Prior Publication Data
US 2012/0006226 A1  Jan. 12, 2012

(30) Foreign Application Priority Data

Mar. 3, 2009 (CH) .......................... 324/09

(51) Int. Cl.
*C09D 103/00* (2006.01)
*A61K 9/48* (2006.01)
(Continued)

(52) U.S. Cl.
CPC .............. *A61K 9/4816* (2013.01); *A61J 3/077* (2013.01); *B29C 43/003* (2013.01); *B29C 43/44* (2013.01); *B29C 43/48* (2013.01); *C08L 3/00* (2013.01); *B29C 2043/486* (2013.01); *B29K 2003/00* (2013.01); *C08L 3/02* (2013.01); *C08L 3/04* (2013.01); *C08L 3/08* (2013.01)

(58) Field of Classification Search
None
See application file for complete search history.

(56) References Cited

U.S. PATENT DOCUMENTS 3,098,492 A   7/1963   Wurtzburg et al.
3,661,154 A   5/1972   Torr
(Continued)

FOREIGN PATENT DOCUMENTS

CN    1324620    12/2001
CN    1432356    7/2003
(Continued)

OTHER PUBLICATIONS

Pushpadas et al, Effects of Extrusion Temperature and Plasticizers on the Physical and Functional Properties of Starch Films, 2008, Starch/Stärke 60, pp. 527-538.*
(Continued)

*Primary Examiner* — Melvin C Mayes
*Assistant Examiner* — Stefanie Cohen
(74) *Attorney, Agent, or Firm* — John B. Hardaway, III; Nexsen Pruet, LLC

(57) ABSTRACT

A method for producing starch films comprises the following steps: preparing a mixture comprising starch and water, wherein more than 50 weight percent of the starch is present in the form of particles of granular starch; shaping the mixture to form a film in a shaping process; solidifying the mixture by increasing the temperature of the mixture during and/or after the shaping process by more than 5° C. Films produced by this method have starch particles bonded to one another. A device for performing this method comprises a shaping device for enabling shaping of the starch material to form a film, and has a heating device for performing a heat treatment for destructuring of the starch during and/or after the shaping.

12 Claims, 5 Drawing Sheets

(51) Int. Cl.

| | | |
|---|---|---|
| *A61J 3/07* | (2006.01) | |
| *B29C 43/00* | (2006.01) | |
| *B29C 43/44* | (2006.01) | |
| *B29C 43/48* | (2006.01) | |
| *C08L 3/00* | (2006.01) | |
| C08L 3/02 | (2006.01) | |
| C08L 3/04 | (2006.01) | |
| C08L 3/08 | (2006.01) | |

(56) References Cited

U.S. PATENT DOCUMENTS

| | | | |
|---|---|---|---|
| 4,454,268 A * | 6/1984 | Otey et al. | 524/47 |
| 5,342,626 A | 8/1994 | Winston et al. | |
| 5,342,646 A | 8/1994 | Kleese et al. | |
| 5,409,973 A | 4/1995 | Bastioli et al. | |
| 5,439,953 A | 8/1995 | Ritter et al. | |
| 6,375,981 B1 | 4/2002 | Gilleland et al. | |
| 6,489,386 B1 * | 12/2002 | Plotzker et al. | 524/291 |
| 6,528,088 B1 | 3/2003 | Gilleland et al. | |
| 6,770,293 B2 | 8/2004 | Angel et al. | |
| 6,790,495 B1 | 9/2004 | Tomka et al. | |
| 6,949,256 B2 | 9/2005 | Fonkwe et al. | |
| 2003/0104048 A1 | 6/2003 | Patel et al. | |
| 2003/0215585 A1 | 11/2003 | Bunick | |
| 2004/0087669 A1 | 5/2004 | Hausmanns et al. | |
| 2007/0275024 A1 | 11/2007 | Hedly et al. | |
| 2009/0068333 A1 | 3/2009 | Muller et al. | |
| 2011/0319503 A1 | 12/2011 | Muller et al. | |

FOREIGN PATENT DOCUMENTS

| | | |
|---|---|---|
| CN | 1486687 | 4/2004 |
| DE | 19943604 A1 | 3/2001 |
| EP | 0118240 A2 | 9/1984 |
| EP | 0546538 A1 | 6/1993 |
| EP | 0546539 A1 | 6/1993 |
| EP | 0735080 A2 | 2/1996 |
| EP | 1335710 | 8/2003 |
| JP | 2003-055198 | 2/2003 |
| JP | 2005-112849 | 4/2005 |
| JP | 2005-170929 | 6/2005 |
| WO | WO 01/03677 A1 | 1/2001 |
| WO | WO 2004/085483 A2 | 10/2004 |
| WO | WO 2007/128150 A1 | 1/2007 |
| WO | WO 2008/105662 A1 | 9/2008 |
| WO | WO 2010/100196 | 9/2010 |

OTHER PUBLICATIONS

Lai L S et al: "Physichchemical Changes and Rheological Properties of Starch During Exttrusion (a Review)" Biotechnology Progress, American Institute of Chemical Engineers, US LNKD-DOI: 10.1021/BP00009A009, vol. 7, No. 3, Jan. 1, 1991, Relevant to claim No. 1-10.
ISSN: 8756-7938 2. Physicochemical Changes in Starch during Extrusion, Relevant to claim No. 15,16H.A. Pushpadas et al.: "Macromolecular Changes in extruded Starch-Films Plasticized with Glycerol, Water and Stearic Acid" Starch/Srärke, vol. 61, May 13, 2009, pp. 256-266, XP002591655 DOI: 10.1002/star. 200800046 2. Materials and Methods, Relevant to claim No. 15-16, 1.
D. Peressini et al: "Starch-Methylcelluose based ediable films; rheological properties of film-forming dispersions" Journal of Food Engineering, vol. 59, 2003, pp. 25-32, XP002591656 the whole document. Relevant to claim No. 16.
IB, International Search Report, PCT/EP2010/052717, Jul. 13, 2010.
Roy L Whistler et al. (Editors): "Starch: Chemistry and Technology", 1984, Academic Press, Inc., Orlando, Seiten 292 and 666.
International Preliminary Report on Patentability PCT/NL2008/050120, Sep. 1, 2009 IB, International Search Report, PCT/NL2008/050120, May 13, 2008.
Lai et al., Physicochemical Changes and Rheological Properties of Starch during. Extrusion (A Review), Biotechnol. Prog. 1991, 7, 251-266, relevant to claims 15 and 16.
Thomas et al., "Gelatinization, Pasting and Retrogradation", Starches: Eagan Press Handbook Series, 1997, Ch. 3, pp. 1-5, Eagan Press, St. Paul, Minnesota.

\* cited by examiner

STARCH FOILS AND/OR FILMS AND A METHOD AND USE OF A DEVICE FOR THE PRODUCTION THEREOF

The present invention relates to a method, in particular a casting method, for producing starch foils and/or sheeting and/or films, the resulting foils and/or sheeting and/or films as well as a device for producing the inventive foils and/or sheeting and/or films.

STATE OF THE ART

Foils and/or films and other molded parts based on starch have long been of special interest because of their biodegradability. However, casting methods for producing molded starch parts from aqueous starch solutions are limited by the low starch content and the high water content of such solutions. Solutions of starch typically become so viscous, even at a starch content of 5%, that simple casting methods at least are no longer possible. The reason for this is the very high molecular weight of starch which may be up to 100,000,000 g/mol.

By degrading starch by cooking and thus reducing the molecular weight, solutions with starch in higher concentrations can be cast, but then inferior mechanical properties of the films and other molded parts are obtained because the long starch macromolecules have a positive influence on the mechanical properties. For example, WO 01/92400 A2 describes cast starch films. The starch used is boiled under conditions which lead to complete destruction of the starch grains.

However, starch films are usually obtained by extrusion, which requires expensive extruders. A homogeneous starch melt of a high viscosity is obtained from starch, which is typically in granular form, at temperatures usually higher than 100° C. with the action of mechanical energy in the form of shearing, which is pressed through a slotted nozzle, for example, under high pressure to produce a starch film. Due to the high mechanical energy input the molecular weight of the starch is greatly reduced, which is a disadvantage for the mechanical properties of the film, and furthermore, the macromolecules become oriented in the longitudinal direction of the film in the flow processes taking place in the nozzle, so that the film is anisotropic which is a disadvantage for further processing. In the extrusion of starch films after shaping the temperature in the film decreases, so the strength of the film increases.

Films produced from homogeneous starch compositions obtained by extrusion are disclosed, for example, in EP 0 735 080 A2 and U.S. Pat. No. 4,454,268 and EP 1,103,254 B1.

Destructuring of starch is obtained by heating starch in an aqueous medium, wherein the destructuring increases with an increase in temperature. If the starch grains are at the same time subjected to mechanical stress by shearing forces, then a higher destructuring is obtained at the same temperature. If the crystallinity of the starch grains is substantially destroyed, then even minor shearing forces such as those which occur in simple mixing and flow processes of starch mixtures are sufficient to increase the degree of destructuring and to substantially destroy the swollen starch grains, and furthermore, the molecular weight of the starch macromolecules can be significantly reduced. The degree of destructuring can be subdivided into the following stages:
stage 1: the crystallinity of the starch is partially destroyed; in a polarization microscope are
stage 1.1: at most 5% of the grains no longer birefringent
stage 1.2: 5-10% of the grains no longer birefringent
stage 1.3: 10-20% of the grains no longer birefringent
stage 1.4: 20-30% of the grains no longer birefringent
stage 1.5: 30-40% of the grains no longer birefringent
stage 2: the crystallinity of the starch is substantially destroyed; in a polarization microscope are
stage 2.1: 40-50% of the grains no longer birefringent
stage 2.2: 50-60% of the grains no longer birefringent
stage 2.3: 60-80% of the grains no longer birefringent
stage 2.4: 80-100% of the grains are no longer birefringent
stage 3: at most 5% of the grains are birefringent
stage 3.1: and 1-10% of the grains have ruptured
stage 3.2: and 10-20% of the grains have ruptured
stage 3.3: and 20-30% of the grains have ruptured
stage 3.4: and 30-50% of the grains have ruptured
stage 3.5: and 50-70% of the grains have ruptured
stage 3.6: and 70-100% of the grains have ruptured
Ruptured starch grains are characterized in that the starch grains have tears/cracks at the surface and/or the previously relatively smooth surface has definitely been deformed (e.g., shrunken surface). In addition to starch particles which are still present as whole grains also starch particles that have disintegrated into fragments may be present. However, the starch grains as well as the fragments are still discernible as entities.
stage 4: no birefringence is observed and the starch grains are substantially destroyed
stage 4.1: there are still fragments of starch grains but the starch is mostly in dissolved form
stage 4.2: the starch is completely in dissolved form There is not a uniform understanding of the term "destructured starch" in the technical world. A destructured starch here refers to a starch which has been destructured at most to stage 4.1, i.e., the starch is still at least partially in the form of particles.

All starch films produced from solutions of degraded starch or extruded starch materials have in common the fact that the molecular weight of the starch is greatly reduced and the starch particles are essentially completely destroyed. Consequently, films produced according to the above-mentioned publications EP 0 735 080 A2, U.S. Pat. No. 4,454, 268 and EP 1,103,254 B1 contain essentially only starch of destructuring stage 4.2.

The object of the present invention is to provide foils and/or sheeting and/or films based on unobjectionable and favorable plant raw materials having good mechanical properties which are simple and cost-effective in production.

DESCRIPTION OF THE INVENTION

This object is achieved according to the invention by a method for producing a foil and/or a film based on starch, in particular by a casting method, in which a mixture comprising starch, in which more than 50 weight percent (wt %) of the starch in the liquid phase is present as particles of granular starch, is shaped into a film, and the mixture is solidified during and/or after this shaping by an increase in temperature, in particular by more than 5° C.

This object is preferably achieved by a method for producing a film based on starch, in particular a casting method, comprising the following steps:
preparing a mixture comprising:
a) >40 weight percent of the dry mixture, after subtracting the plasticizer, starch, wherein more than 50 weight percent of the starch in the liquid phase is present in the form of particles of granular starch,
b) 0-70 weight percent of the dry mixture plasticizer,
c) 15-90 weight percent of the total mixture water, d) optionally at most 50 weight percent of the dry mixture, after subtracting the plasticizer, thickener, and e) optionally conventional additives and adjuvants, shaping the mixture to form a film in a shaping operation, solidifying the mixture by increasing the temperature of the mixture during and/or after the shaping operation by more than 5° C. to form a compact film comprising particles of destructured starch, optionally drying the film.

According to the invention, the molecular weight of the starch is not impaired significantly. Therefore, especially good mechanical properties of the fresh and dry film are possible. In addition, however, also the heterogeneous structure of the material contributes significantly to this in that the destructured particles of granular starch formed at the solidification temperature already have a certain strength and elasticity per se, which has advantageous effects on the handling of the fresh film in further processing.

For good mechanical properties of the starch film, the molecular weight of the starch and its proportional amount in the starting mixture should be large enough. The initially contradictory combination of pourability, i.e., low viscosity, and high molecular weight of the starch is achieved according to the invention by the fact that in the casting mixture the starch is present in the form of particles. Then the viscosity of the mixture is determined primarily by the viscosity of water and plasticizer and is low accordingly. For example, a starch mixture comprising approximately 35 weight percent water in total and 35 weight percent glycerol, based on the starch content, can be cast well, even without pressure. A mixture of the same composition but in which the starch is present in destructured, dissolved or plasticized form prior to shaping would have a viscosity at least 1000 times higher, i.e., more than 10,000 Pas. To shape such a mixture to form a film, high pressures would be needed such as those which can be produced by extruders, for example. Alternatively the water content of such a mixture would have to be increased to approximately 95% in order for the mixture to be castable without pressure. However, then it would still be a liquid after casting even with a subsequent temperature increase and not a film with usable mechanical properties.

If the starch mixture is heated, increasing swelling and destructuring of the starch particles occur, wherein the particles incorporate water and plasticizer, swell and stick together. An agglomerate or conglomerate of particles is obtained, i.e., a heterogeneous structure consisting of a mixture of starch particles.

Solidification of the castable mixture which previously had a low viscosity to form a viscoelastic solid material which can be characterized by a typical solid-state property such as the modulus of elasticity then occurs almost simultaneously with the increase in temperature and occurs due to the fact that the liquid phase of water and plasticizer disappears, i.e., diffuses into the starch particles, a network structure, i.e. a gel structure within the starch particles is formed due to the entanglement of macromolecules, and the particles are stuck to one another. Optionally, the sticking of the particles can still be modified by adding a thickener.

Solidification of the mixture is understood to refer to the primary solidification wherein there is a destructuring of granular starch, i.e., a phase conversion of the starch and the properties of the mixture change by orders of magnitude. This phase conversion is manifested as gellation of the casting compound/casting material to form a solid film. This does not require any other gelling agents besides starch. After the primary solidification of the mixture there is a secondary solidification which is accompanied by a gradual change in the properties of the substance when the temperature of the film, which has solidified primarily, and/or its water content is/are reduced and/or a gradual formation of a network of the starch occurs, induced by retrogradation, i.e., crystallization of the starch macromolecules.

According to the invention, mixtures of starch with high starch proportions can be processed to films using simple casting methods. In comparison with a mixture in which the same amount of starch is present in dissolved form, lower viscosities of the mixture are obtained by several orders of magnitude. Solidification of the mixture to an isotropic film material of a high elasticity and high extensibility is achieved through an increase in temperature. It is advantageous that the molecular weight of the starch is not impaired significantly in the inventive method. Preferably the $M_w 2/M_w 1$ quotient is >0.3, more preferably >0.4, more preferably >0.5, more preferably >0.6, more preferably >0.7, more preferably >0.8, where $M_w 1$ is the weight-average molecular weight distribution of the starch used and $M_w 2$ is the weight-average molecular weight distribution of the starch in the film produced. It should be noted here that the molecular weight of starch shows a very sensitive reaction to mechanical stress. For example, the molecular weight of dissolved starch is measurably reduced merely by shaking the solution.

The starch mixtures to be used according to the invention may be processed to films in almost the same way as is the case with gelatin-casting methods. This is an especially favorable prerequisite for replacing gelatin films because the same installations and equipment can be used. The difference in comparison with gelatin films from the standpoint of the process technology consists essentially of the fact that gelatin melts will undergo gelling when cooled whereas the inventive starch mixtures undergo gelation due to an increase in temperature.

In a preferred embodiment, the film has an upper limit pertaining to the thickness in mm of 10, preferably 5, more preferably 3, more preferably 2, more preferably 1.5, more preferably 1.0, most preferably 0.9. With a decrease in thickness, the increase in temperature for solidification is facilitated, in particular if the increase in temperature is achieved substantially by thermal conduction, and the reduction in water content in the film after solidification is also facilitated.

In a preferred embodiment, the film has a lower limit pertaining to the thickness in mm of 0.001, preferably 0.01, more preferably 0.05, even more preferably 0.1, more preferably 0.2, and most preferably 0.3. With an increase in the thickness of the film, its ease of handling is facilitated.

Starch

Generally any starches or mixtures thereof may be used with regard to the origin and processing. For example, they may be used in the native state as well as in a physically and/or chemically/enzymatically modified state.

With regard to the origin, root starches, for example, potato starches or tapioca starches are preferred because they have low gelatinization temperatures in comparison with starches of other origin and the solidification and/or gelation of the casting composition to form films is therefore possible even at low temperatures. Tapioca starch is especially preferred. Tapioca starch is colorless, tasteless, has a very good transparency and no genetically modified variants of tapioca starches are known.

In a preferred embodiment, the starch is used in the native, i.e. unmodified state. Good properties can be achieved at a low cost in this way.

In another preferred embodiment, substituted starches such as starch esters and starch ethers are used, for example, hydroxypropylated or acetylated starches. These modifications lead to especially high transparency and high extensibility of the film.

Oxidized starches are used as an alternative.

In another preferred embodiment, crosslinked starched are used, in particular crosslinked starch esters and/or crosslinked starch ethers, for example, starch phosphates and starch adipates. By increasing the molecular weight, which is associated with crosslinking, improved mechanical properties are obtained and the starch grains are also stabilized mechanically as units, which is especially advantageous for the process because the contribution of the starch particles to the mechanical properties of the fresh film and of the dry film can be increased in this way. In the case of highly crosslinked starches, the destructured starch grain practically forms a molecule of a gigantic molecular weight and has a particularly high stability.

In another preferred embodiment, substituted tapioca starch is used, in particular crosslinked substituted tapioca starch, for example, hydroxypropylated starch phosphate.

The preferred weight-average molecular weight distribution $M_w1$ of the starch that is used is at least 500,000 g/mol, especially preferably at least 1,000,000 g/mol, more preferably at least 2,500,000 g/mol, even more preferably at least 3,000,000 g/mol, even more preferably at least 4,000,000 g/mol, even more preferably at least 5,000,000 g/mol, even more preferably at least 7,000,000 g/mol, most especially preferably at least 10,000,000 g/mol.

The amylose content of the starches in weight percent is preferably <50, more preferably <40, more preferably <35, more preferably <30, more preferably <27, more preferably <25, most especially preferably <20. High amylose contents lead to a reduced extensibility of the film and the film is of a lower quality with respect to gloss and transparency. Furthermore, its disintegration properties in an aqueous medium are worsened.

In addition waxy starches, in particular crosslinked and/or substituted waxy starches are preferred. Waxy starches are advantageous with regard to transparency.

According to the invention the starch is preferably not of the C structure type (i.e., leguminous starch, for example) because corresponding starches lead to inferior elongation properties of the film, but is of the A and/or B structure type.

In one embodiment of the invention, the starch source is selected from native or modified starches of the A and/or B structure type, in particular from the group consisting of tapioca starch, potato starch and mixtures thereof and waxy starches, wherein modified tapioca starch, in particular substituted tapioca starch and most especially preferably substituted and crosslinked tapioca starch or modified potato starch or substituted potato starch or substituted and crosslinked potato starch are especially preferably used.

The amylose content of the starches in weight percent is preferably >=0, more preferably >0.3, more preferably >0.5, more preferably >0.7, more preferably >1, more preferably >2, most especially preferably >3. If the amylose content is too low it may lead to reduced extensibility of the film.

Also preferred are starches with a gelatinization temperature <90° C., especially preferably <80° C., more preferably <75° C., more preferably <70° C., more preferably <67° C., most especially preferably <65° C. The gelatinization temperature is determined by DSC (differential thermal calorimetry) as the peak temperature in heating a starch/water mixture comprising 65 weight percent of water at a rate of 10° C./min. With a decline in gelatinization temperature, the solidification of the cast film at lower temperatures becomes possible and thus both easier and faster.

Starches with a dextrose equivalent (DE) of <10, especially preferably <1, most preferably <0.7, more preferably <0.5, more preferably <0.2, more preferably <0.1, most especially preferably <0.05 are also preferred. The dextrose equivalent of a polysaccharide mixture refers to the percentage amount of reducing sugar in the dry substance. It corresponds to the amount of glucose (=dextrose), which would have had the same reducing power per 100 g dry substance. The DE value is a measure of how far the degradation of the polymer has proceeded, so all products with a low DE value have a large amount of polysaccharides and a small amount of low molecular sugars (oligosaccharides) whereas products with a high DE value consist mainly only of low-molecular sugars. The dextrose equivalent is determined according to ISO standard 5377. The strength of the film increases after solidification as the DE value becomes lower.

In a preferred embodiment of the invention, the starch content of the dry mixture, after subtracting the plasticizer (i.e., after mathematical subtraction of the plasticizer from the dry mixture consisting of starch, plasticizer and all the optional components) in weight percent is >40, especially preferably >50, more preferably >60, more preferably >70, more preferably >80, more preferably >90, especially preferably >95.

Granular Starch

The granular starch is preferably used with a destructuring of up to 2.2, more preferably up to stage 2.1, more preferably up to stage 1.5, more preferably up to stage 1.4, more preferably up to stage 1.3, more preferably up to stage 1.2, more preferably up to stage 1.1, most especially preferably in the native undestructured state. The viscosity of the mixture declines with a decline in destructuring, so that the casting is simplified.

According to the invention, the granular starch is used in the form of particles, these particles corresponding in their shape to the original starch grains or being agglomerates thereof. Typical sizes of the starch grains in the unswollen state are 5-100 μm for potato starch, 5-30 μm for corn starch, 1-45 μm for wheat starch, 4-35 μm for tapioca starch, 1-30 μm for rice starch. In a partial destructuring, the original starch grains may have been altered with regard to geometry and size, in particular with a definite increase in size in destructuring. As granular starch also mixtures of various granular starches may be used.

The amount of granular starch in weight percent in the total starch content of the mixture is preferably >60, especially preferably >70, more preferably >75, more preferably >80, more preferably >85, most especially preferably >90.

Water

Water is important in adjusting the viscosity of the casting compound and in solidification of the film after shaping the casting composition to form a film. The greater the water content, the simpler is the casting, the more rapidly is the solidification and the less is the temperature increase required to accomplish this. On the other hand, a high water content reduces the strength of the film and longer drying times are needed because then more water must be removed from the film.

The upper limit for the water content of the casting composition in weight percent is preferably 90, especially preferably 80, more preferably 70, more preferably 60, more preferably 50, more preferably 45, most especially preferably 40, while the lower limit of the water content of the casting composition in weight percent is preferably 15, especially preferably 20, more preferably 25, more preferably 30, most especially preferably 33. With an increase in the water content, solidification is facilitated, e.g., made possible and/or accelerated at lower temperatures, but the strength of the solidified film is reduced and the amount of water that must be removed again after solidification is increased.

Plasticizer

Generally all the plasticizers for starch known in the state of the art may be used as the plasticizer. A low plasticizer content leads to embrittlement of the film at low atmospheric humidity levels, whereas a high plasticizer content leads to inferior properties at a high atmospheric humidity.

Plasticizers may be used individually or in mixtures of various plasticizers. Polyols such as glycerol, sorbitol, maltitol, erythritol, xylitol, mannitol, galactitol, tagatose, lactitol, maltulose, isomalt, maltol, etc. are preferably used, but also various sugars such as sucrose, maltose, trehalose, lactose, lactulose, galactose, fructose, etc. as well as mono- and oligosaccharides. Glycerol is especially preferred as a plasticizer. In addition to its property as a plasticizer, sucrose also has the advantage that it improves the oxygen barrier properties of the film. Water is also a plasticizer for starch but is not counted with the plasticizers here and is taken into account separately.

The upper limit for the plasticizer content in weight percent of the dry mixture preferably amounts to 70, especially preferably 60, more preferably 55, more preferably 50, more preferably 46, most especially preferably 42, whereas the lower limit in weight percent is preferably 0, especially preferably 5, more preferably 10, more preferably 15, more preferably 20, more preferably 25, more preferably 28, more preferably 31 more preferably 32.5, most especially preferably 33.5.

In a preferred embodiment, plasticizers with a maximum melting point of the anhydrous plasticizer of 150° C., preferably 125° C., especially preferably 110° C., more preferably 95° C., most especially preferably 70° C. are used. The amount of plasticizer in the total plasticizer content which meets this condition is in weight percent >50, preferably >70, especially preferably >80, most especially preferably >90.

Optional Components of the Starch Mixture

Short-Chain Amylose

The starch mixture may comprise an amount of short-chain amylose. This short-chain amylose may be obtained in the granular starch, for example, by the action of enzymes on the granular starch or may be applied to the granular starch by spraying the granular starch with dissolved short-chain amylose. This short-chain amylose may be supplied together with at least one of the starches which is used to prepare the film or it may be added separately to the mixture, for example, in the form of a solution of short-chain starch or in the form of spray-dried short-chain starch, where the spray-dried short-chain starch may have other spray-dried starches than those in the mixture. The short-chain amylose is preferably present in and/or on the granular starch in non-crystalline form.

Short-chain amylose consists of substantially unbranched amyloses and is used in a preferred embodiment. The degree of branching (number of branches per monomer unit) of the short-chain amyloses is <0.01, preferably <0.005, especially preferably <0.003, more preferably <0.001, more preferably <0.0007, more preferably <0.0004, most especially preferably <0.0001. Ideally the short-chain amylose has a degree of branching of 0 or close to zero, for example, when it is obtained by complete debranching (for example, by means of pullulanase). With the decline in the degree of branching, the crystallizability of the short-chain amylose and thus also the formation of a network (by heterocrystallization with longer starch macromolecules) increases, which is effected by the short-chain amylose. With an increase in formation of network, improved properties of the inventive film are obtained, in particular higher modulus of elasticity values at high atmospheric humidities, so that the film can be used in a wide range of climate zones with different atmospheric humidities.

Short-chain amylose has an average degree of polymerization (DPn: number-average) of >8 and <500. According to the invention it is preferably <300, especially preferably <100, more preferably <70, more preferably <50, most especially preferably <30. In addition it is preferred according to the invention that the average degree of polymerization is >10, especially preferably >12, more preferably >14, most especially preferably >15. With a decline in DPn the transparency of the film is improved because the heterocrystallites consisting of short-chain amylose and longer starch macromolecules become smaller with a decrease in the DPn of the short-chain amylose so that the light scattering is reduced. If the DPn is too low crystallization is no longer possible.

Short-chain amylose can be obtained, for example, by polymerization of glucose synthetically or from starch by the action of enzymes (for example, α-amylase, β-amylase, isoamylase, pullulanase).

The amount of short-chain amylose in the total starch content of the mixture in weight percent is preferably <15, especially preferably <10, more preferably <7.5, more preferably <5, more preferably <3, most especially preferably =0.

Thickeners

A thickener may be added to the mixture comprising starch to adjust the viscosity of the mixture at a desired level, so it permits optimization of the viscosity of the mixture in casting. Furthermore, thickeners are advantageously used to weaken the bonds between the destructured starch particles in the solidified film with regard to an accelerated decomposition behavior in an aqueous medium. The thickener may be present in the form of particles, in swollen form or in dissolved form at the time of shaping of the mixture.

Generally all hydrophilic substances and mixtures thereof may be used as thickeners if they increase the viscosity, in particular hydrophilic polymers and of those, preferably those of plant sources. Examples include hydrocolloids and gums such as galactomannans, e.g., guar gum or locust beam gum; cellulose derivates, in particular cellulose ethers; pectins, in particular rhamnogalacturonans and protopectins; dextrans; xanthan; zymosan; hydrocolloids from marine algae, such as alginates, agar, agarose, carrageen and carrageenans; furcellaran; hydrocolloids from lichens, such as lichenins and isolichenins or hydrocolloids as exudates from woods, such as gum tragacanth (astragalus gum), karaya gum, gum arabic, kutira gum; inulin; latex; chitin; chitosan; gellan; collagen; gelatin; casein. Dissolved starch may be used for the same function as the thickeners but it is not counted with the thickeners and is treated separately.

Some of these thickeners, for example, gelatin, carrageenan, gellan and pectin are also known as gelling agents, but they gel when cooled instead of when heated. They do not make any contribution toward gelation in the solidification of the inventive casting mixture with an increase in temperature, nor are they used for this purpose.

In a preferred embodiment, the maximum amount of thickener in weight percent, based on the dry recipe, after subtracting the plasticizer is 50, more preferably 40, more preferably 30, more preferably 20, more preferably 10, more preferably 5, more preferably 2.5, most especially preferably 1.

In another preferred embodiment, the maximum amount of carrageen and carrageenans in weight percent, based on the dry recipe, after subtracting the plasticizer is 10, more preferably 7.5, more preferably 5, more preferably 3, more preferably 2, more preferably 1, more preferably 0.5, most especially preferably 0. Because of the high cost of raw materials and the suspected carcinogenicity, the amount of carrageen and carrageenans is kept as low as possible.

In another preferred embodiment the maximum amount of gelatin in weight percent, based on the dry recipe, after subtracting the plasticizer is 10, more preferably 7.5, more preferably 5, more preferably 3, more preferably 2, more preferably 1, more preferably 0.5, most especially preferably 0. Because of the general gelatin problems, the amount of gelatin is kept as low as possible.

In another preferred embodiment the maximum amount of gellan in weight percent, based on the dry recipe, after subtracting the plasticizer is 5, more preferably 2.5, more preferably 2, more preferably 1.5, more preferably 1, more preferably 0.5, more preferably 0.2, most especially preferably 0. The amount of gellan is kept as low as possible because of the high cost of raw materials.

In another preferred embodiment the maximum amount of pectin in weight percent, based on the dry recipe, after subtracting the plasticizer is 5, more preferably 2.5, more preferably 2, more preferably 1.5, more preferably 1, more preferably 0.5, more preferably 0.2, most especially preferably 0. The amount of pectin is kept as low as possible because of the high cost of raw materials and the problems in processing.

In another preferred embodiment the maximum amount of cellulose derivatives in weight percent, based on the dry recipe, after subtracting the plasticizer is 15, more preferably 10, more preferably 5, more preferably 2.5, more preferably 1, more preferably 0.5, most especially preferably 0. The amount of cellulose derivatives is kept as low as possible because of the high cost of raw materials and the separation and/or precipitation of cellulose derivatives from the starch mixture at increased temperatures.

Dissolved Starch

Dissolved starch may be used like the thickeners mentioned above to increase the viscosity of the mixture and to modify the bond between the starch particles. Its use is optional because the desired increase in viscosity to a viscosity suitable for casting can also be achieved through a suitable increase in the temperature of the casting mixture, where the granular starch increases the viscosity due to swelling. However, the temperature of the casting mixture must be adjusted and controlled accurately so the procedure when using dissolved starch (or a thickener) is simpler and is therefore preferred.

With regard to dissolved starch, the same statements apply as with regard to suitable starches and preferred types such as those pertaining to starch in general. However, dissolved starch may also have a lower molecular weight than is generally preferred for the starch. Furthermore, highly retrogradation-stabilized starches, for example highly substituted starches or highly branched dextrins, are also preferred for the dissolved starch so that the disintegration of the film in an aqueous medium can be accelerated.

Dissolved starch differs from granular starch in its condition in the casting mixture where it is present in dissolved form or in a predominantly destructured form while the granular starch at this point in time is still primarily not destructured.

Dissolved starch may be obtained, for example, by dissolving amorphous extruded starch or it may be obtained from pregelatinized starch. According to the invention the term "dissolved starch" is also understood to include pregelatinized starch (such as, for example, roll-dried pregelatinized starch) even if this is present in undissolved form or is only partially dissolved. Pregelatinized starch is preferably destructured at least to stage 2.3, more preferably at least to stage 2.4, even more preferably at least to stage 3.1, even more preferably at least to stage 3.3.

In a preferred embodiment, dissolved starch is destructured at least to stage 2.3 at the latest by the time when the mixture is shaped into a film, even more preferably at least to stage 2.4, more preferably at least to stage 3.1, more preferably at least to stage 3.3, more preferably at least to stage 3.5, more preferably at least to stage 3.6, especially preferably at least to stage 4.1, most especially preferably up to stage 4.2.

In addition it is preferable according to the invention for the upper limit for the amount of dissolved starch based on the anhydrous mixture in weight percent to be 30, especially preferably 25, more preferably 20, more preferably 15, more preferably 10, most especially preferably 5.

Additional Components (Additives and Adjuvants)

Additional components of the starch mixture may include dyes and pigments as well as fillers, mineral fillers, for example, talc, or modifying substances such as polyethylene glycols or disintegration aids, for example, carbonates or bicarbonates or additives, for example, preservatives, antioxidants or emulsifiers, for example, lecithins, mono-, di- and triglycerides of fatty acids, polyglycerol esters, polyethylene esters or sugar esters. Generally all additives which are used in extruded starch films may also be used according to the invention. If fibers are used (inorganic or organic fibers), then the maximum amount in weight percent, based on the dry recipe after subtracting the plasticizer, is preferably <15, especially preferably <10, more preferably <5, more preferably <2.5, more preferably =0. Fibers have a negative effect on the very good elongation properties of the film.

Shaping and Solidification

The starch in the form of particles of granular starch is destructured during and/or after the shaping of the mixture to form a film by an increase in temperature so that rapid solidification of the casting mixture to form a solid film is obtained.

The temperature increase preferably takes place after the mixture is shaped to form a film, in particular immediately after the shaping of the mixture to form a film. The temperature increase during the shaping optionally amounts to at most 50%, preferably at most 40%, more preferably at most 30%, more preferably at most 20%, most preferably at most 10% of the total temperature increase of the casting compound to the solidification temperature.

In a preferred embodiment, the mixture comprising starch may be shaped under a pressure of less than 5 bar (0.5 MPa), especially preferably less than 4 bar (0.4 MPa), more preferably less than 3 bar (0.3 MPa), more preferably less than 2 bar (0.2 MPa), most especially preferably less than 1 bar (0.1 MPa). At such pressures the pressure buildup is simple and the equipment required is also simple and favorable. In yet another preferred embodiment the mixture comprising starch may be shaped at a pressure of less than 0.7 bar (0.07 MPa), especially preferably less than 0.6 bar (0.06 MPa), even more preferably less than 0.5 bar (0.05 MPa), more preferably less than 0.4 bar (0.04 MPa), more preferably less than 0.3 bar (0.03 MPa), most especially preferably less than 0.2 bar (0.02 MPa). In the most preferred embodiment the mixture is shaped under practically no pressure, i.e., the mixture flows due to its inherent weight through the shaping unit which is a spreader box, for example, which is the standard equipment used in casting gelatin.

The viscosity of the casting mixture may generally also be set so high, with thickeners for example, that pressures far above 5 bar (0.5 MPa) are necessary for shaping the casting mixture to form a film.

The upper limit for the dynamic viscosity of the mixture before or during shaping (i.e., the viscosity at the corresponding temperature) in Pas is preferably 3000, especially preferably 1000, more preferably 500, more preferably 300, more preferably 200, more preferably 150, more preferably 120, more preferably 100, more preferably 70, most especially preferably 50. In addition it is preferable for the lower limit for the dynamic viscosity of the mixture before or during shaping in Pas to be 0.01, especially preferably 0.05, more preferably 0.1, more preferably 0.5, most especially preferably 1. The viscosities are based on the shear rate of 1.1/s. High viscosities correlate with the need for high pressures so that the advantages of the low viscosities correspond to the advantages of the lower pressures. Since there are a number of possibilities of shaping mixtures with a wide range of viscosities, the viscosities in question cover a wide range accordingly. In the case of a viscosity below approximately 300 Pas, pressureless casting methods (under the inherent weight of the mixture) by means of the spreader box typically used for the gelatin casting method are possible. The lower limits are defined by the fact that the shaping and in particular the adjustment of the thickness of a cast film become increasingly difficult at very low viscosities (the mixture flows away).

The upper limit for the temperature in ° C. at which the mixture comprising starch is shaped is preferably 90, especially preferably 80, more preferably 70, more preferably 65, more preferably 60, more preferably 55, most especially preferably 50. In addition, in a preferred embodiment, the lower limit for the temperature in ° C. at which the mixture comprising starch is shaped is −20, especially preferably −10, more preferably 0, more preferably 10, more preferably 20, more preferably 30, more preferably 35, more preferably 40, most especially preferably 45.

Starting from the temperature of the casting compound before shaping, i.e., the temperature of the casting compound in the spreader box, the temperature of the starch mixture is increased to solidify it. The lower limit for the temperature increase of the starch mixture in ° C. to induce solidification is preferably 10, especially preferably 15, more preferably 20, more preferably 25, more preferably 30, more preferably 35, most especially preferably 40. In addition, in a preferred embodiment, the upper limit of the temperature increase in ° C. is 130, more preferably 110, more preferably 90, most especially preferably 70. With an increasing temperature increase the solidification is accelerated and better mechanical properties are obtained because the starch particles are better bonded to one another. The upper limit is determined by the bubbling which occurs and/or increases with an increase in temperature.

The water content after shaping the casting compound during the solidification of the product is preferably kept approximately constant, in particular until the film (at room temperature) has reached an modulus of elasticity in MPa of at least 0.001, preferably 0.003, especially preferably 0.005, more preferably 0.007, more preferably 0.009, most especially preferably 0.01. During the solidification the water content is preferably reduced by at most 25 weight percent, especially preferably by at most 20 weight percent, more preferably by at most 15 weight percent, more preferably by at most 10 weight percent, more preferably by at most 7 weight percent, more preferably by at most 5 weight percent, most especially preferably by at most 3 weight percent (for illustration: the water content after shaping the casting compound to form a film is 40%, so the water content after a 3% reduction is 37%). The constancy of the water content during solidification of the film facilitates the solidification but if the water content is reduced too greatly during this phase it leads to incomplete solidification of the film and thus to inadequate mechanical properties and in particular the film then tends to develop tears and cracks in further processing.

Films

Inventive films based on starch preferably include:
a) >40 weight percent of the dry film after subtracting the plasticizer, starch,
b) 0-70 weight percent of the dry film plasticizer, and
c) 0.1-50 weight percent of the total film water,
d) optionally at most 50 weight percent of the dry film, after subtracting the plasticizer, thickener, and
e) optionally conventional additives and adjuvants,
where the film comprises starch particles bonded to one another, in particular particles of destructured starch bonded to one another. The starch particles bonded to one another preferably form a matrix, and additional phases are optionally included in this matrix. The amount of additional phases in weight percent is preferably <30, more preferably <20, more preferably <10, more preferably <5, more preferably <2.5, most preferably <1.5.

In a preferred embodiment the inventive film is in one layer during solidification, i.e., in this phase of the process no additional layers which are bonded to the film and remain bonded to it are present.

These starch particles in the films are destructured starch particles formed from granular starch in gelation of the casting mixture to form the film, and destructured starch particles that were already in this state before gelation of the casting mixture and originated from the dissolved starch (where their degree of destructuring preferably corresponds at least to that of the granular starch) may optionally also be present.

The starch particles of the granular starch preferably still exist as individual starch particles, especially with an average diameter of at least 2 μm, more preferably at least 4 μm, more preferably at least 6 μm. The starch particles formed from granular starch are preferably destructured at least to stage 2.1, especially preferably up to stage 2.2, more preferably up to stage 2.3, more preferably up to stage 2.4, most especially preferably up to stage 3.1. With an increase in destructuring, the handling of the fresh film and the mechanical and optical properties of the dry film are improved. On the other hand the starch particles are preferably destructured at most up to stage 4.1, especially preferably up to stage 3.6, more preferably up to stage 3.5, more preferably up to stage 3.4, more preferably up to stage 3.3, most especially preferably up to stage 3.2. To achieve a very high destructuring, very high temperatures are necessary in solidification, which is complicated to monitor and control in terms of the process engineering, in particular control of the water content as well as the formation of unwanted air bubbles. Furthermore, at a very high degree of destructuring, when the starch grains are increasingly disintegrating, the positive contribution of the starch particles to the mechanical properties of the fresh film and of the dry film decline.

The granular starch is present as solid, at most partially swollen particles at the time of shaping of the mixture to yield a film. This starch is present in the solidified film in the form of severely swollen destructured starch particles which are bonded together either directly by coupling of surfaces of such particles or indirectly via an intermediate layer, where this intermediate layer may optionally comprise a binder and/or starch, in particular dissolved starch. The ratio of the average thickness of the intermediate layer divided by the average diameter of the swollen particles is preferably <0.4, especially preferably <0.2, more preferably 0.15, more preferably <0.1, more preferably <0.05. In other words the particles are preferably densely packed, most preferably the particles come in contact with one another in a dense packing, in particular in an extremely dense packing (i.e., a packing without intermediate spaces).

The bond between the starch particles may optionally be improved by the dissolved starch between the particles or by another binder, but an adequate bond is achieved even without this measure. The structure of the starch film as a dense agglomerate of particles is clearly manifested when the film is placed in water and moved with a magnetic stirrer, for example, at room temperature or at 70° C. The film disintegrates, optionally under the influence of a slight rubbing (at room temperature), initially to form a fine uniform paste. If this material is further diluted with water, individual starch particles may again be obtained from it and can be identified by their shape under a light microscope as swollen particles of destructured starch. The origin and/or type of starch used can even be determined from destructured starch grains which can be recovered from the film because different starches have different grain shapes and grain size distributions. To make the particles visible under the microscope, they are advantageously stained with an iodine solution (Lugol's solution). Another possibility of revisualizing the original starch particles is placing one drop of the material diluted with water on a microscope slide instead of staining. After the water has evaporated, the starch particles can be identified under the light microscope. Because of the shrinkage of the swollen starch particles in drying, these particles have characteristic deformations and optionally tears.

The preferred weight-average molecular weight distribution $M_w2$ of the comprised starch, like the preferred weight-average molecular weight distribution $M_w1$ of the starch in the starch casting mixture, is at least 500,000 g/mol, especially preferably at least 1,000,000 g/mol, more preferably at least 2,500,000 g/mol, even more preferably at least 3,000,000 g/mol, more preferably at least 4,000,000 g/mol, more preferably at least 5,000,000 g/mol, more preferably at least 7,000,000 g/mol, most especially preferably at least 10,000,000 g/mol.

With regard to the ingredients of the film, except for the water content, statements regarding the casting mixture used in the method are applicable. The upper limit for the water content of the inventive film in weight percent is preferably 40, especially preferably 30, more preferably 25, more preferably 20, most especially preferably 17, while the lower limit of the water content of the film in weight percent is preferably 1, especially preferably 3, more preferably 5, most especially preferably 7. As the water content increases, the film loses its mechanical properties, and in particular becomes too soft. The film becomes too hard as the water content is lower.

Insoluble Components of the Film

The films that are produced consist of particles of starch which are packed densely in a preferred embodiment, which yields advantageous properties for the processing of the film and for the properties of the finished film. These particles of starch can be separated, for example, from the soluble components (which include in particular plasticizer, soluble starch, optionally thickeners) by dissolving the film at 70° C. for 30 minutes, and their quantitative amount in the film can thus be measured.

Recovery Method No. 1

In a preferred embodiment, the minimal amount in weight percent of the starch in the film which can be recovered after dissolving the film at 70° C. for 30 min is 30, preferably 40, more preferably 50, more preferably 55, more preferably 60, more preferably 65, most especially preferably 70%.

Recovery Method No. 2

In another preferred embodiment the amount of the material which can be recovered after dissolving the film at 70° C. for 30 min is determined and is based on the mass of the dry film. The determination according to this definition is simpler than that according to recovery method no. 1 because it can also be used when the composition of the film is not known exactly. The minimal amount in weight percent of the material which can be recovered is 25, preferably 35, more preferably 40, more preferably 45, most especially preferably 50.

Use of the Films

Films produced with the inventive method are used as a substitute for gelatin films.

Another use is the use in the field of packaging materials, in particular as sachets, capsules, bags, pockets and bags. The films are especially suitable for use in the field of packaging materials that disintegrate in water, for example, water-disintegrating packaging materials, in particular portion bags for perfumes and cleaning agents, in particular for detergents.

Another use is in the field of biodegradable packagings. Another use is the use in the field of films which are applied to the skin. In this form of application, ingredients may also be present in the film accordingly.

Another use is the use as a face mask. In this form of application, cosmetic ingredients may also be present in the film, for example.

Another inventive use of the film is that the dried film, which comprises little or no plasticizer in particular, is pulverized to yield particles. In particular these particles have an average particle size in the range of 0.01 to 0.2 mm. These particles may then be used advantageously in the field of confectionary production as gelling agent, in particular for gummy bonbons and jellies, where the particles are preferably used in the so-called low-temperature Mogul method according to WO 2007/128150 A1. In this field, improvements can be achieved with the particles obtained from the inventive film with regard to texture, processability, and the spectrum of the products produced.

Advantages of the Inventive Method and the Inventive Film

Inventive casting mixtures are simple to produce. No extruders are needed but instead a simple casting process may be used. In particular pressureless casting under inherent weight is also possible. Due to the rapid solidification (gelation) after casting, high and competitive production rates are obtained. The film is also isotropic in contrast with extruded films, i.e., its properties no longer depend on direction. Extruded films must be heat-treated to reduce the anisotropy but then also they are hardly completely isotropic.

The essential feature of the starch mixture which is used in the inventive method is that this mixture comprises starch in the form of particles, i.e., the mixture is a dispersion of the particles in an aqueous medium. This mixture is stable over a long period of time.

The fresh film may have a modulus of elasticity of at least 0.009 MPa and an elongation at break of at least 100% after solidification. The modulus of elasticity and elongation at break are measured at room temperature, immediately after solidification, i.e., at most a few minutes after shaping the mixture to form a film, where the water content corresponds to the water content after solidification of the film. If solidification is achieved on a rotary drum, for example, then the modulus of elasticity and the elongation at break of the film are measured after the film has left the drum and the water content in the measurement corresponds to the water content of the film at this point in time. Handling of the film becomes possible only when the modulus of elasticity is high enough and the elongation at break is adequate after solidification because the solidified film is subjected to mechanical stress in the further processing. The properties of the fresh film are more than adequate for this so that high production rates are also possible.

Inventive films also have good mechanical properties, in particular a high elasticity and high extensibility. The films are composed of densely packed individual starch particles which are bonded to one another/interconnected. These starch particles are present in a swollen state and preferably in a dense packing. The films are also compact and free of air bubbles. In the past it has been assumed by the technical world that the starch must be plasticized in the extruder for usable films, but then the individuality of the starch particles used, typically granular starch, is completely lost.

In view of the particulate structure, where one would first expect the bonds between the starch particles to be weak points, it is even more surprising that the inventive film actually has better mechanical properties, for example, a higher modulus of elasticity than a film of the same composition which was produced by plasticizing the starch in an extruder. The reason for this lies at least partially in the fact that the molecular weight of the starch macromolecules is reduced during plasticization of starch due to the high temperature and/or the high shearing, and the mechanical properties increase with the molecular weight. Since no shearing is needed to produce the inventive film and the temperatures required are definitely lower than those in plasticization, the molecular weight of the starch in the film corresponds approximately to the molecular weight of the starch before processing (molecular weight determinations usually include a substantial error because the measurements are difficult).

Known films of plasticized starch become soft when stored in water but retain more or less dimensional stability and disintegrate into fragments under mechanical stress. There is no dissolving in the original starch particles because their identity has been destroyed in plasticization by extrusion. However, inventive films in water break down into the starch particles of which they are composed and thus exhibit an advantageous disintegration behavior as is required for soluble packaging materials.

Since the particles of the film are densely packed, it has a high density. It is preferably in the range of 1.07-1.3 g/cm³.

When using casting compounds which do not comprise any additives, such as pigments to reduce transparency, the casting compound, which comprises starch particles and therefore is almost completely opaque, becomes increasingly transparent to the degree as solidification progresses. After conclusion of solidification the film is then almost completely transparent. This means that writing that is just barely legible for a person at a distance can still be read by this person at the same distance when it is covered with a transparent film (approximately 0.5 mm thick) and the character size has been increased by at most 50%.

Inventive films are stable over a wide range of atmospheric humidity and temperature. The good mechanical properties of the inventive film are a result of the structure of the film as an agglomerate of densely packed destructured starch grains as well as being a result of the high molecular weight of the starch which is made possible through the inventive method. The destructured starch grains have a certain strength and therefore make a contribution to the good mechanical properties of the film in a wide range of atmospheric humidity.

Device for Producing Films Based on Starch

An inventive device for producing films based on starch comprises the following equipment: a shaping device to enable shaping of a starch material to form a film, at least one heating device to perform a heat treatment for gelation of the starch during and/or after the shaping as well as optionally a drying device downstream from the heating device. The inventive device for producing films optionally also comprises a device for regulating the water content of the film during and/or after the shaping, in particular during the solidification of the starch in the area of the heating device.

In the inventive method it is preferably cast on a rotating part of the process, and the increase in temperature of the casting compound takes place there, in particular through thermal conduction. Generally, however, alternatively or additionally any other type of heating may be used, but in particular heating methods using radiation are suitable, for example, infrared radiation or microwave radiation. Other heating methods use water vapor. The rotating part of the process is preferably a drum. Another implementation is a revolving belt, for example.

The film preferably remains in contact with the rotating part of the process until the film has essentially solidified completely (primary solidification).

In a preferred embodiment, the film remains in contact with the rotating part of the process for at least 30% of the circumference of the rotating part of the process, especially preferably for at least 40%, more preferably for at least 50%, more preferably for at least 60%, most especially preferably for at least 70%.

In a preferred embodiment, the device for regulating the water content of the film regulates the water content so that the water content of the film is reduced during contact with the rotating part of the process by at most 25 weight percent, especially preferably by at most 20 weight percent, more preferably by at most 15 weight percent, more preferably by at most 10 weight percent, more preferably by at most 7 weight percent, more preferably by at most 5 weight percent, most especially preferably by at most 3 weight percent (for illustration: the water content after shaping the casting compound to form a film is 40% so after reduction of 3% it is 37%).

In a preferred embodiment, the rotating part of the process can be heated to a temperature of at least 25° C., especially preferably at least 50° C., more preferably at least 80° C., more preferably at least 90° C., more preferably at least 100° C., most preferably at least 105° C.

The rotating part of the process preferably has thermal insulation on at least one side.

The device for regulating the water content of the film after shaping in a preferred embodiment comprises a means covering the film on the rotating part of the process for at least 30% of the circumference, especially preferably for at least 40%, more preferably for at least 50%, more preferably for at least 60%, most especially preferably for at least 70%. The water content in the film is thus regulated during solidification, in particular being kept essentially constant.

This cover is preferably achieved by a corotational belt, which rests on the film and in particular has the same speed or angular velocity as the rotating part of the process. This belt may have its own drive, but is preferably driven directly with the rotating part of the process, so that the transfer of force between the rotating part of the process and/or the film and the belt is accomplished by means of adhesion. The belt may be heated before it comes to lie on the rotating part of the process and/or the film, for example, heated by radiation such as infrared radiation. Along the circumference of the belt around the rotating part of the process in the area where the belt lies on, another or several heating devices may be used, for example, infrared lamps.

The device for regulating the water content of the film after shaping in another preferred embodiment comprises a means for restricting the space above the film along at least a portion of the rotating part of the process so that the volume wherein water evaporates out of the film is limited. This restriction preferably pertains to at least 30% of the circumference of the rotating part of the process, especially preferably at least 40%, more preferably at least 50%, more preferably at least 60%, most especially preferably at least 70%. The restricted volume preferably amounts to at most 10 times the volume of the film within the restriction, especially preferably at most 5 times, more preferably at most twice. In a preferred embodiment, the restricted volume is climatized, i.e., atmospheric humidity and optionally temperature are regulated.

The device for regulating the water content of the film after shaping in another preferred embodiment comprises a means for supplying water to the film, preferably hot water, especially preferably water vapor.

The device for regulating the water content of the film after shaping in another preferred embodiment comprises a means for covering the surface of the film with a liquid. In particular the means produces a film of the liquid on the starch film or the means comprises a bath of the liquid through which the starch film is passed. The liquid is preferably an oil.

EXAMPLES

The recipes for the examples are shown in Table 1. Casting mixtures of 10 kg each were prepared. The viscosity of the casting mixture, the mechanical properties and the recovery of the starch are also shown in Table 1.

In all the attempts to prepare starch films, completely transparent films of a good quality were obtained.

In all the inventive examples, microscopic analysis revealed that the starch films were constructed of densely packed destructured starch grains (<5% birefringent starch grains) and the films could be dissolved into these components again in water, i.e., after disintegration of the films, the destructured starch grains could be detected again in water and their weight could be determined (recovery method no. 1).

Disintegration of the films in water was determined in an agitated bath at 25° C. on films which had been dried to a water content of approximately 10% after preparation and were then stored for 20 days at 33% atmospheric humidity. The films dissolved after less than 20 min in all examples.

Example 1

According to recipe 1, the water and plasticizer were first added to a heatable and evacuable vessel equipped with a stirrer at room temperature and these two components were then mixed at 100 rpm. Next starch S1E which was extruded under very gentle conditions at a water content of 35% was added and dissolved in the mixture of water and plasticizer for 5 min at 100 rpm. The extruded starch S1E was prepared from dry extrudate (based on the starch S1) by means of a beater mill and had a particle size distribution in the range of 30-150 μmm, as well as a 10% short-chain amylose content (this short-chain amylose was obtained from tapioca starch by complete debranching by means of pullulanase and had a number-average of the degree of polymerization $DP_n$ of 25).

To this mixture was then added the granular starch S1 which had a weight-average molecular weight $M_w$ of 30,100,000 g/mol and dispersed therein at 100 rpm for 5 min after which this mixture was heated to 45° C. and degassed for 5 min at 100 rpm by applying a vacuum (removing air bubbles). The dynamic viscosity of this mixture at this temperature was 5.7 Pas at a shear rate of 1.1/s.

Figure 1:
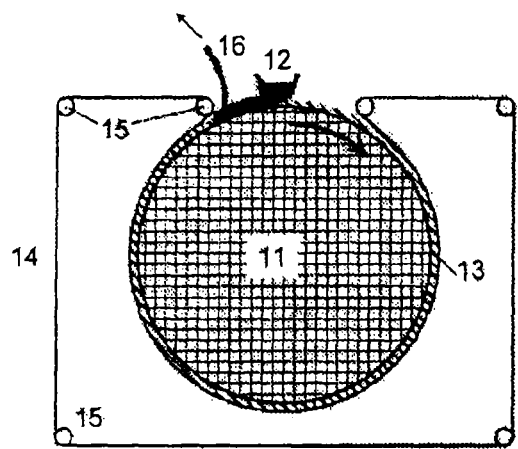
FIG. 1 shows a detail of a first embodiment of the inventive device for producing films.
Figure 2:
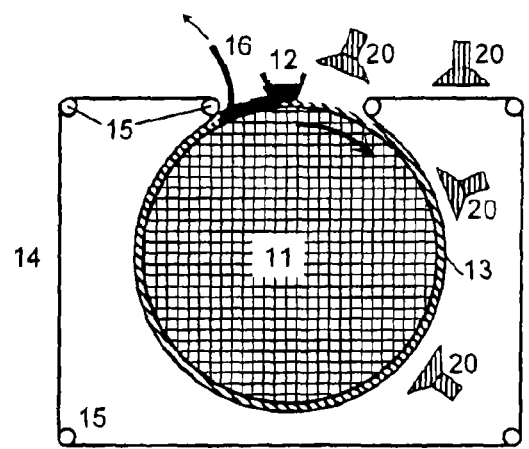
FIG. 2 shows a detail of a second embodiment of the inventive device for producing films.

The hot mixture was then processed by means of an inventive casting device to form a film. This device is illustrated in FIG. 1. It comprises a rotating heated drum (11), a spreader box (12), a revolving Teflon belt (14) and pulleys (15). The casting compound (13) is solidified to form a film (16).

The drum (11) consists of a metal cylinder with a diameter of 50 cm which was heated to the temperature TZ of 105° C. by means of a heating fluid. The rotational speed n of the drum was 0.6 revolution per minute. The casting temperature TG of the mixture was 45° C. The mixture was cast to form a film (16) with a width of 25 cm and a thickness of 0.7 mm by means of the spreader box (12) on the rotating metal cylinder. Along ¾ of the circumference the cast film (16) was covered by the corotating Teflon belt (14), so that the water content in the film would remain constant. After a ¾ revolution the film was detached from the metal cylinder and sent to a drying apparatus. The resulting films were completely transparent. No birefringent starch grains were observed in the films. The mass temperature of the film on the drum after ¾ revolution was 91° C.

Figure 3:
FIG. 3 shows a light microscopic image of an inventive starch film according to Example 1, which was stored at a relative atmospheric humidity of 58%, in a magnification of 1:150 (a film detail with a width of 0.57 mm is shown).
Figure 4:
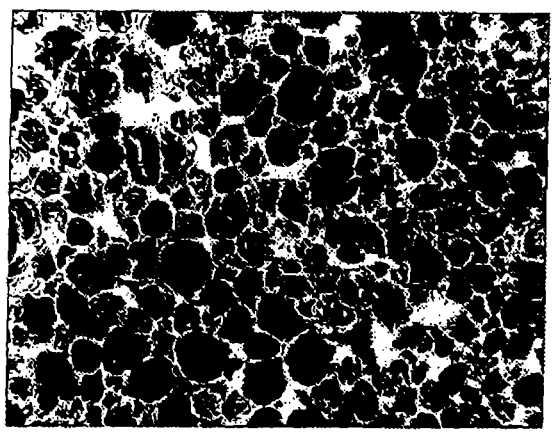
FIG. 4 shows a light microscopic image of an inventive starch film according to Example 1 with a magnification factor of 150, which was stored at a relative atmospheric humidity of 58% (a film detail with a width of 0.57 mm is shown).
Figure 5:
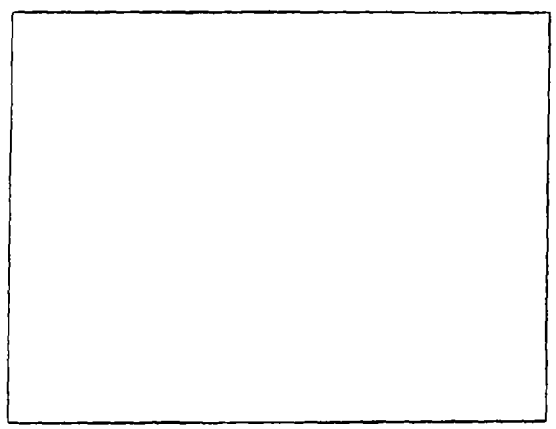
FIG. 5 shows a light microscopic image of an extruded starch film not according to the invention with a magnification factor of 150 (a film detail with a width of 0.57 mm is shown).

A light microscopic image of a starch film which was stored over sodium bromide for 7 months (relative atmospheric humidity 58%) is shown in FIG. 3. This shows clearly that the film consists of interconnected starch grains. FIG. 4 shows a light microscopic image of a starch film which was stored for 7 months over magnesium chloride (relative atmospheric humidity 33%). For comparison an extruded starch film according to European Patent EP 1 103 254 B1 is shown in FIG. 5. All the starch particles were destroyed by extrusion, so they can no longer be detected in the light microscope.

The modulus of elasticity values of films from Example 1, which were stored for 2 weeks at relative atmospheric humidities of 33%, 43%, 57% and 75%, were 23 MPa, 3.4 MPa, 3.7 MPa and 3.3 MPa, whereas the modulus of elasticity values of films having the same composition but produced by extrusion (in the longitudinal direction) were 4.5 MPa, 0.7 MPa, 0.9 MPa and 0.4 MPa at the same atmospheric humidities.

Example 1a

Example 1 was repeated. The extruded starch S1E and the granular starch were mixed together with the mixture of water and plasticizer. It was found that the sequence in preparation of the casting mixture had no effect on further processing or product properties.

Example 1b

Example 1 was repeated. The finished casting mixture was stored for two hours at room temperature before further processing without having any effect on the further processing or the product property.

Example 1c

Example 1 was repeated. The finished casting mixture was stored for two hours at 45° C. before further processing without having any effect on further processing or the product property.

Example 2

Like Example 1, but instead of 38% water the casting compound had a water content of 35%. The temperature of the drum was set at 108° C. The mass temperature of the film on the drum after ¾ revolution was 93° C.

Example 3

Like Example 1, but instead of 38% water the casting compound had a water content of 41.1%. The temperature of the drum was set at 103° C. The mass temperature of the film on the drum was 89° C. at ¾ revolution.

Example 4

Like Example 1, but the amount of extruded starch S1E in the casting compound was increased from 2.28% to 4.49% so that the dynamic viscosity at 45° C. and a shear rate of 1.1/s increased from 5.7 Pas to 21 Pas. The temperature of the drum was set at 105° C. The mass temperature of the film on the drum was approximately 90° C. at ¾ revolution.

Example 5

Like Example 1, but the hydroxypropylated crosslinked tapioca starch S1 was replaced by the native tapioca starch S2, and the starch S1E was replaced by the pregelatinized starch S2P. The temperature of the drum was set at 111° C. The mass temperature of the film on the drum after ¾ revolution was approximately 96° C.

Figure 12:
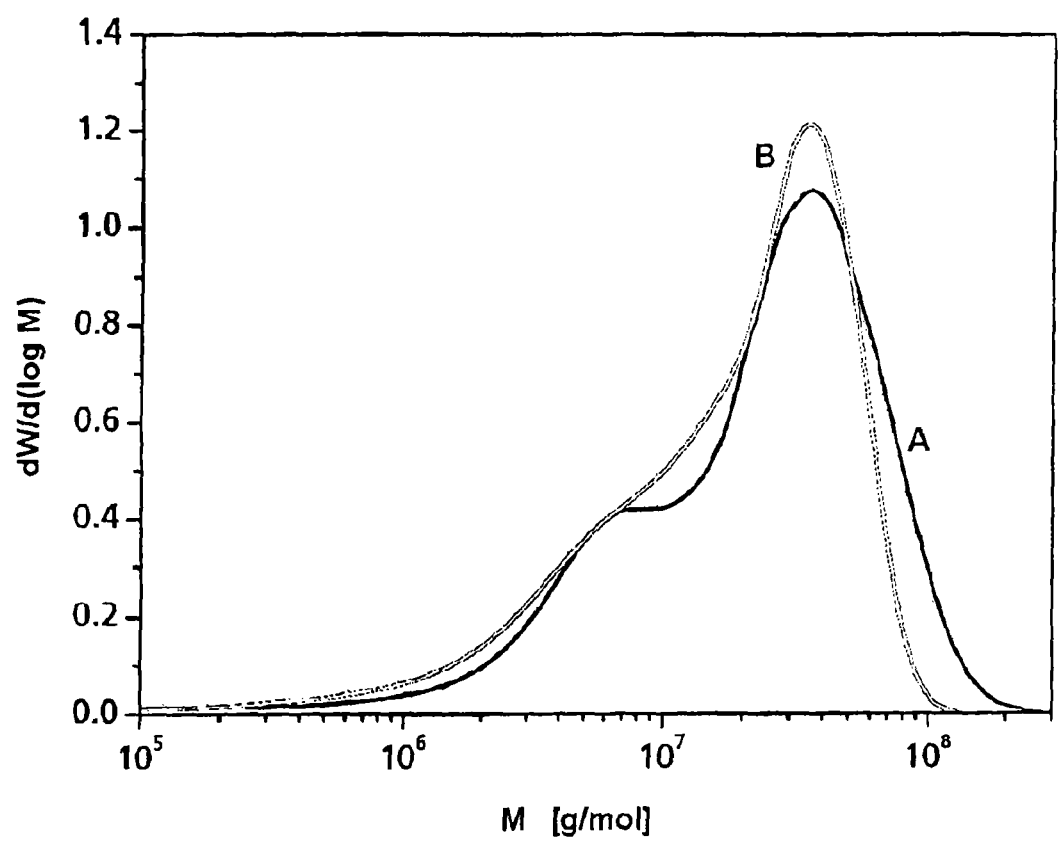
FIG. 12 shows the molar-mass distributions of a starting starch and a starch recovered by dissolving an inventive film according to Example 5 which was produced from this starting starch.

Before processing, the starches S2 and S2P had a weight-average molecular weight $M_w$ of 22,690,000 g/mol and the starch extracted from the film produced therewith had a molecular weight $M_w$ of 21,340,000, i.e., the molecular weight was only minimally reduced in production (cf. FIG. 12).

Example 6

Like Example 1, but the glycerol content was increased. The temperature of the drum was set at 102° C. The temperature of the film after ¾ revolution was 88° C.

Example 7

Like Example 1, but the hydroxypropylated crosslinked tapioca starch S1 was replaced by the native waxy potato starch S4. The temperature of the casting mixture was 40° C. The temperature of the drum was set at 102° C. The temperature of the film after ¾ revolution was 87° C.

Example 8

Like Example 1, but the hydroxypropylated crosslinked tapioca starch S1 was replaced by the hydroxypropylated potato starch S5, and the starch S1E was replaced by the pregelatinized hydroxypropylated potato starch S5P. The temperature of the casting mixture was 40° C. The temperature of the drum was set at 101° C. The temperature of the film after ¾ revolution was 86° C.

The starches S5 and S5P had a weight-average molecular weight $M_w$ of 13,530,000 g/mol before processing and the starch extracted from the film produced therewith had a molecular weight $M_w$ of 13,490,000 at a first measurement, 15,460,000 at a second measurement, i.e., the molecular weight underwent practically no change in production of the film. The apparent increase in molecular weight in the second measurement could be attributed to the fact that the accuracy of molecular weight measurements is limited at these high molecular weights.

Example 9

Like Example 1, but the extruded starch S1E was replaced by the pregelatinized starch S1P.

The starches S1 and S1P have a weight-average molecular weight $M_w$ of 30,100,000 g/mol. The molecular weight analysis of the starch in the corresponding films revealed a molecular weight $M_w$ of 21,340,000 g/mol in a first measurement and a molecular weight $M_w$ of 20,220,000 g/mol in a second measurement, i.e., the molecular weight was reduced only slightly by the process. In particular in comparison with the extrusion method where the starch S1 had a molecular weight $M_w$ of only 920,000 g/mol, although it was extruded under the gentlest possible conditions, i.e., at a high water content and low shear rates.

Example 9a

Example 9 was repeated. But, the extruded starch S1E was replaced by the starch S1 (as dissolved starch) and after adding this starch S1 to the mixture of water and plasticizer, this starch S1 was destructured in this mixture by heating to 90° C. After subsequent cooling to a temperature below 45° C., the granular starch S1 was then added (as granular starch). This had no effect on the following process and the product properties.

Example 9b

Example 9a was repeated. To avoid cooling, the method was simplified by destructuring the starch S1 (as dissolved starch) only in a portion of the water-plasticizer mixture and then adding the rest of water and plasticizer at room temperature to lower the temperature to below 45° C.

Example 10

Like Example 9. But the pregelatinized starch S1P was replaced by the pregelatinized starch S6P. Here again the same procedures could be used as those described in Examples 9a and 9b in order to destructure the starch S6 (as dissolved starch).

Examples 11 to 13

Like Example 1. But in these examples, the dissolved starch S1E was replaced by thickeners V1, V2 and V3 so that the disintegration behavior of the films in an aqueous medium could be accelerated. To dissolve the thickeners V2 (xanthan gum) and V3 (locust bean gum) in the mixture of water and plasticizer, the mixture of water, plasticizer and polysaccharide was heated to 90° C. as in Example 9a and was then cooled to a temperature below approximately 45° C. before adding the granular starch. Here again, the same variant can be used as in Example 9b to prevent active cooling of the mixture of water, plasticizer and dissolved polysaccharide.

Examples 14 to 16

Like Example 1. But in these examples, the dissolved starch S1E was replaced by various tapioca dextrins S7, S8 and S9, so that the disintegration behavior of the starch films in an aqueous medium could be accelerated. To dissolve the dextrins S7 and S8 in the mixture of water and plasticizer, the mixture of water, plasticizer and polysaccharide was heated to 90° C. according to Example 9a and then cooled to a temperature below approximately 45° C. before adding the granular starch (starch 1 according to Table 1). Here again, the same variant can be used as in Example 9b to prevent active cooling of the mixture of water, plasticizer and starch.

Example 17

With all the starch films obtained from Examples 1 through 17, the original starch particles could be recovered by placing them in water and visualized under a microscope by staining using Lugol's solution.

Figure 6:
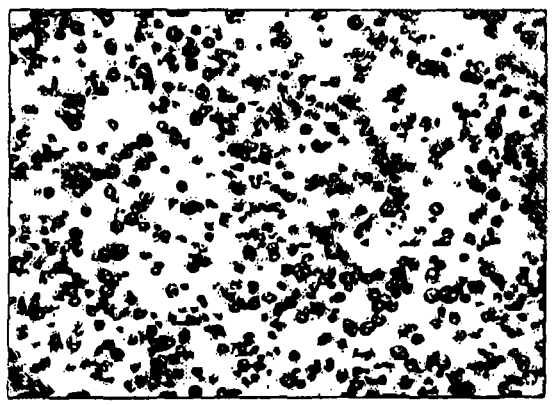
FIG. 6 shows a light microscopic image of an aqueous suspension of unprocessed, bifringent hydroxypropylated tapioca starch with a magnification factor of 150 (a detail with a width of 0.57 mm is shown).

A light microscopic image of the unprocessed granular tapioca starch S1 from Example 1 is shown in FIG. 6.

Figure 7:
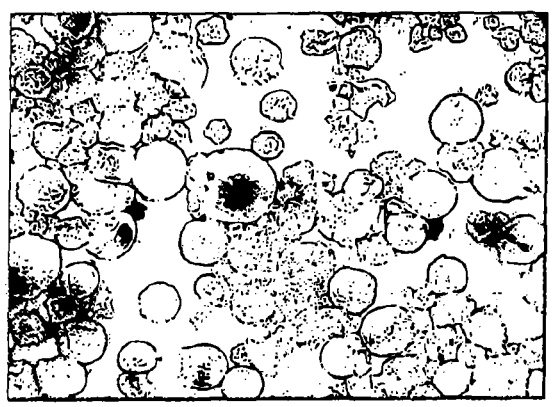
FIG. 7 shows a light microscopic image of an aqueous suspension of hydroxypropylated tapioca starch which was heated to 70° C., with a magnification factor of 150 (a detail with a width of 0.57 mm is shown).

FIG. 7 shows the change in this starch under the influence of temperature. The sample was prepared by suspending 20 weight percent starch in water in a test tube and heating for 5 minutes at 70° C. in a water bath. After cooling to room temperature, the starch was stained with iodine and examined under a microscope. Although FIG. 6 shows small birefringent starch particles, it can be seen that the particles in FIG. 7 are swollen and no longer show any birefringence.

Figure 8:
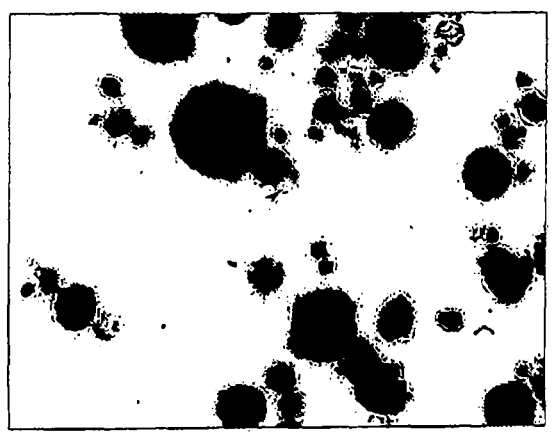
FIG. 8 shows a light microscopic image of an aqueous suspension of hydroxypropylated tapioca starch obtained by heating an inventive film according to Example 1 in water to 70° C., with a magnification factor of 150 (a detail with a width of 0.57 mm is shown).

FIG. 8 shows starch particles recovered from starch films. To do so, a starch film from Example 1 was first stored for 7 months over magnesium chloride (relative atmospheric humidity: 33%). A sample was prepared by keeping approximately 100 mg of the film in 7 g water while stirring with a magnetic stirrer for 30 min at 70° C., whereupon the material disintegrated into particles. After cooling, staining with iodine was performed. These starch particles from the film are stained more and are more dilute but do not differ significantly from those in FIG. 7 which were obtained by heating the suspended starch. It has thus been demonstrated that the film consists of destructured starch grains.

Example 18

Example 17 was repeated with the potato starch S5 and the films according to Example 8.

Figure 9:
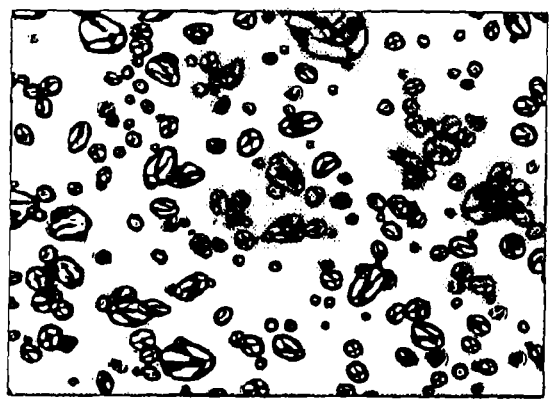
FIG. 9 shows a light microscopic image of an aqueous suspension of unprocessed hydroxypropylated potato starch under crossed polarizers, with a magnification factor of 150 (a detail with a width of 0.57 mm is shown).

A light microscopic image under crossed polarizers of the unprocessed starch S5 from Example 8 is shown in FIG. 9. The larger grains are a good illustration of the Maltese cross known to be typical of native starch.

Figure 10:
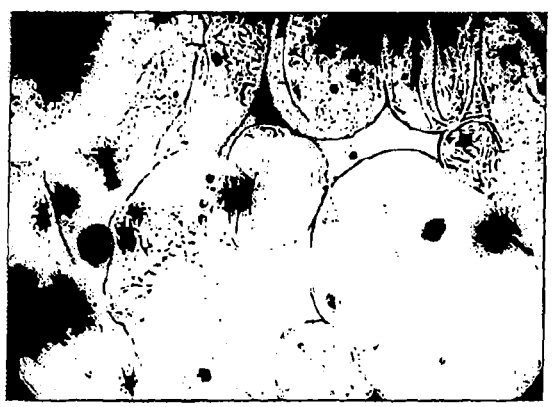
FIG. 10 shows a light microscopic image of an aqueous suspension of hydroxypropylated potato starch which was heated to 70° C., with a magnification factor of 150 (a detail with a width of 0.57 mm is shown).
Figure 11:
FIG. 11 shows a light microscopic image of an aqueous suspension of hydroxypropylated potato starch which was obtained by heating a sample of an inventive film according Example 5 in water to 70° C., with a magnification factor of 150 (a detail with a width of 0.57 mm is shown).

FIG. 10 shows the change in this starch after heating to 70° C. FIG. 11 shows starch particles recovered from films according to Example 8, stored 7 months over sodium bromide (relative atmospheric humidity: 58%).

They are like the starch grains in FIG. 10 but have stronger staining and are more dilute. This demonstrates that the film consists of destructured starch grains that can be converted to a suspension and can be recovered by sedimentation.

Example 19

FIG. 3 shows a light microscopic image of an inventive starch film according to Example 1. A very thin layer of the starch film was sliced off with a razor blade and one drop of iodine solution was placed on it (the dark locations were stained more strongly). This preparation was then pressed by hand between two microscope slides to reduce the thickness of the film somewhat more. The resulting film thickness had approximately the thickness of two starch grains so the grains were partially situated one above the other. Nevertheless it is readily discernible that the film consists of a dense packing of destructured starch grains (no more birefringence was discernible).

FIG. 4 shows a light microscopic image of an inventive starch film according to Example 1. To visualize the individual starch grains more clearly in comparison with FIG. 3, the starch film obtained with the razor blade was swollen briefly at 70° C., the starch grains were stained with iodine and the film was pressed by hand between two microscope slides so that the film thickness corresponded approximately to the thickness of the grains. The grains are swollen due to the swelling at 70° C. and therefore are somewhat larger than those in FIG. 3.

Example 20

FIG. 5 shows a light microscopic image of an extruded starch film not according to the invention with a magnification factor of 150 (a film detail with a width of 0.57 mm is shown). Since the starch has dissolved completely, no more particles of starch are present. A mass content of approximately 1.5% of the dry film was obtained by recovery method 2, which could be sedimented from the solution and can be attributed to insoluble additives.

Example 21

The molar-mass distributions of the unprocessed starch S2 and the starch S2 that was processed to yield a film according to the invention according to Example 5 were compared with one another. To do so, the starch film was dissolved by pressure-cooking under defined conditions in a mini autoclave and the molar-mass distribution of the molecularly dispersely dissolved starch was investigated by means of GPC-MALLS.

To do so, the starch samples were suspended in water with a concentration of 3 weight percent dry substance. This suspension was heated while stirring in a mini autoclave. After reaching 150° C., the temperature was maintained for 20 minutes. The solution was next cooled to 60° C., diluted to 0.3 weight percent, filtered through a 5 µm membrane filter and measured on the GPC-MALLS.

The resulting molar-mass distributions are shown in FIG. 12, where A denotes the sample of the starting starch S2 and B denotes the starch of the film sample according to example 5. The average molar-mass of the starting starch is found to be MW=22.69×106 g/mol and the molar-mass of the starch recovered from the film is found to be MW=21.84×106 g/mol. It can be ascertained that the relatively high molar-mass of the starting sample was not significantly degraded by processing to a film. Starting starch and processed starch were both in a comparable molar-mass range.

Measurement Methods

Dynamic viscosities were determined with the help of a Brookfield viscometer of the type LVDV-I+ at a shear rate of 1.1/s (5 rpm, spindle 25) and the stated temperatures.

The mechanical properties (elongation at break, modulus of elasticity) were measured on an Instron 5542 test system according to ISO 527.

Water contents were measured by drying over phosphorus pentoxide at 80° C. for 48 hours.

The GPC-MALLS was performed by means of an Alliance 2695 separation module from the company Waters, DRIDetector 2414 from the company Waters and a Dawn-HELEOS MALLS detector from Wyatt Technologie Inc., Santa Barbara, USA, at a wavelength l=658 nm and a K5 flow-through cell. Columns: SUPREMA-Gel column set, exclusion limits S30000 with 108-106, S1000 with 2×106-5×104, S100 with 105-103. Eluent: DMSO with 0.09M $NaNO_3$, temperature: 70° C., analysis: Astra Software 5.3.0.18. A refractive index increment do/dc of 0.068 was taken for all samples.

The determination of the insoluble fraction in the film was performed as follows: first the dried film was stored for 2 months at 57% atmospheric humidity. A quantity of 100-150 mg (dry matter M0) in the form of a piece of film of 0.5 mm thickness was swollen and/or dissolved together with 7 g demineralized water at 70° C. in a test tube for 30 min while stirring slowly with a magnetic stirrer. Then the test tube was centrifuged until the undissolved components had sedimented and the supernatant had become clear. The supernatant was then decanted. Next 7 g demineralized water was added and stirred with the sediment then centrifuged again and finally decanted. This procedure was repeated again to be sure that there were no longer any soluble constituents in the sediment. This sediment consisted of undissolved starch in the case of a film consisting of starch and plasticizer. Finally the sediment was dried for 48 hours at 80° C. over phosphorus pentoxide and the dry mass (M1) were determined. The proportion of the mass that could be recovered after the dissolving process was thus obtained as 100×M1/M0 in weight percent. The proportion of starch that can be recovered after the dissolving process is obtained as follows for a starch film consisting of starch and plasticizer as 100×M1/(M0×(1−(WM/100))) in weight percent, where WM is the amount in weight percent of the plasticizer of the dry mixture. As a rule, the starch film still comprises at most minimal amounts of insoluble components, e.g., pigments (typically <0.5%) or fillers such as titanium dioxide (typically <1.5%) in addition to the starch particles. In case of need such components are subtracted from the dry matter M0 and the mass M1.

TABLE 1

| Example | Granular starch | Dissolved starch | Thickener | Recipe of the casting mixture | | | | | | Fresh film | | | | |
| | | | | Granular starch [%] | Dissolved starch [%] | SCA [%] | Thickener [%] | $H_2O$ [%] | WM [%] | Viscosity of the casting mixture [° C.] [Pas] | | Modulus of elasticity [MPa] | Elongation [%] | $H_2O$ [%] | Wg. [%] |
| 1 | S1 | S1E | — | 38.97 | 2.28 | 0.25 | — | 38.0 | 20.5 | 45 | 5.7 | 0.03 | 386 | 36.5 | 86.3 |
| 2 | S1 | S1E | — | 40.85 | 2.39 | 0.27 | — | 35.0 | 21.5 | 45 | 14 | 0.04 | 430 | 34.2 | 87.2 |

TABLE 1-continued

| | | | | Recipe of the casting mixture | | | | | | Fresh film | | | | |
|---|---|---|---|---|---|---|---|---|---|---|---|---|---|---|
| Example | Granular starch | Dissolved starch | Thickener | Granular starch [%] | Dissolved starch [%] | SCA [%] | Thickener [%] | H$_2$O [%] | WM [%] | Viscosity of the casting mixture [°C.] | [Pas] | Modulus of elasticity [MPa] | Elongation [%] | H$_2$O [%] | Wg. [%] |
| 3 | S1 | S1E | — | 37.06 | 2.17 | 0.24 | — | 41.1 | 19.5 | 45 | 2 | 0.02 | 531 | 40.0 | 86.7 |
| 4 | S1 | S1E | — | 36.54 | 4.49 | 0.50 | — | 38.0 | 20.5 | 45 | 21 | 0.03 | 420 | 37.0 | 82.3 |
| 5 | S2 | S2P | — | 38.97 | 2.28 | 0.25 | — | 38.0 | 20.5 | 45 | 2.8 | 0.03 | 452 | 36.8 | 92.1 |
| 6 | S1 | S1E | — | 39.08 | 2.29 | 0.25 | — | 33.5 | 24.9 | 45 | 21 | 0.02 | 510 | 33.1 | 91.5 |
| 7 | S4 | S1E | — | 38.98 | 2.28 | 0.25 | — | 38.0 | 20.4 | 40 | 8 | 0.14 | 148 | 35.8 | 73.4 |
| 8 | S5 | S5P | — | 39.42 | 1.88 | 0.21 | — | 38.0 | 20.5 | 40 | 4.3 | 0.03 | 430 | 36.5 | 64.2 |
| 9 | S1 | S1P | — | 39.43 | 2.09 | — | — | 38.0 | 20.5 | 45 | 11 | 0.04 | 421 | 36.7 | 88.4 |
| 10 | S1 | S6P | — | 39.45 | 2.09 | — | — | 38.0 | 20.5 | 45 | 4 | 0.02 | 523 | 34.3 | 79.5 |
| 11 | S1 | — | V1 | 41.11 | — | — | 0.41 | 38.0 | 20.5 | 45 | 35 | 0.05 | 440 | 37.9 | 89.2 |
| 12 | S1 | — | V2 | 41.32 | — | — | 0.21 | 38.0 | 20.5 | 45 | 17 | 0.04 | 508 | 37.7 | 91.2 |
| 13 | S1 | — | V3 | 41.11 | — | — | 0.41 | 38.0 | 20.5 | 45 | 20 | 0.04 | 467 | 37.8 | 92.5 |
| 14 | S1 | S7 | — | 33.24 | 8.30 | — | — | 38.0 | 20.5 | 45 | 13 | 0.03 | 507 | 37.2 | 88.4 |
| 15 | S1 | S8 | — | 33.23 | 8.30 | — | — | 38.0 | 20.5 | 45 | 10 | 0.02 | 563 | 37.4 | 86.2 |
| 16 | S1 | S9 | — | 36.56 | 5.02 | — | — | 38.0 | 20.5 | 45 | 22 | 0.02 | 499 | 35 | 84.7 |

Legend to Table 1
Granular Starch:
S1 hydroxypropylated crosslinked tapioca starch (Creamtex 75725 from Cerestar)
S2 native tapioca starch (from Cerestar)
S4 waxy potato starch (Eliane 100 from AVEBE)
S5 hydroxypropylated potato starch (Emden KH 15 from Emsland) dissolved starch:
S1E starch S1, extruded, comprising 10% short-chain amylose
S1P starch S1, pregelatinized
S2P starch S2, pregelatinized
S5P starch S5, pregelatinized
S6P hydroxypropylated starch (Emcol H7 from Emsland), pregelatinized
S7 tapioca dextrin (Cleargum TA 90 from Roquette)
S8 tapioca dextrin (Tapioca Dextrin 11 from Tatenyle)
S9 mixture of 50% starch S1P and 50% tapioca dextrin (Dextrin D-400 from Cerestar)
Thickener:
V1 guar gum (Meypro Guar CSAA M-200 from Meyhall/Rhodia)
V2 xanthan gum (Keltrol HP E415 from Kelko)
V3 locust bean gum (Meypro LBG Fleur M-175 from Meyhall/Rhodia)
WM: glycerol as plasticizer
All percentage amounts are given in weight percent based on 100 weight percent of the total casting mixture.
The mechanical properties (modulus of elasticity and elongation) of the fresh film were measured at a temperature of 25° C., 10 min after producing the film.
Wg.: recovery according to recovery method no. 1

The invention claimed is:

1. A casting method for producing a foil and/or film based on starch wherein a mixture comprising starch, in which more than 50 weight percent of the starch in a liquid phase is present as particles of granular starch, which is destructured at most up to stage 2.2, is cast without using an extruder and shaped to form a film and during and/or after this shaping the mixture is solidified by an increase in temperature by destructuring the granular starch,
wherein starch being destructured to stage 2.2 is defined in that 50-60% of the starch grains are no longer birefringent in a polarization microscope.

2. The casting method for producing a foil and/or film based on starch according to claim 1, comprising the following steps:
preparing a mixture, comprising:
a) >40 weight percent of the dry mixture, after subtracting plasticizer, the starch, wherein more than 50 weight percent of the starch in the liquid phase is present as particles of granular starch,
b) 0-70 weight percent of the dry mixture, plasticizer,
c) 15-90 weight percent of the total mixture, water,
d) optionally at most 50 weight percent of the dry mixture, after subtracting the plasticizer, thickener,
e) optionally conventional additives and adjuvants, and
f) 0 weight percent or at most 10 weight percent of the dry mixture, after subtracting the plasticizer, carrageen and carrageenans,
shaping the mixture without using an extruder to form a film and/or foil in a shaping process,
solidifying the mixture by increasing the temperature of the mixture during and/or after the shaping process by more than 5° C., and
optionally drying the film and/or foil.

3. The method according to claim 1 wherein the mixture comprising starch in shaping to form a film and/or foil has a dynamic viscosity of <3000 Pas.

4. The method according to claim 1 wherein the water content of the mixture during the solidification is reduced by at most 25 weight percent.

5. The method according to claim 1 wherein the molecular weight of the starch is not significantly impaired and an $M_w2/M_w1$ quotient is >0.3, where $M_w1$ is the weight-average molecular weight distribution of the starch used and $M_w2$ is the weight-average molecular weight distribution of the starch in the film and/or foil produced.

6. The method according to claim 2 wherein the mixture comprising starch in shaping to form a film has a dynamic viscosity of <3000 Pas.

7. The method according to claim 2 wherein the water content of the mixture during the solidification is reduced by at most 25 weight percent.

8. The method according to claim 2 wherein the molecular weight of the starch is not significantly impaired and an $M_w2/M_w1$ quotient is >0.3, where $M_w1$ is the weight-average molecular weight distribution of the starch used and $M_w2$ is the weight-average molecular weight distribution of the starch in the film and/or foil produced.

9. The method according to claim 2 wherein the mixture comprises 5-70 weight percent of the dry mixture, plasticizer.

10. The method of claim 1 wherein the temperature is increased by more than 5° C. to solidify the mixture.

11. The method of claim 1 wherein the weight-average molecular weight distribution $M_w2$ of the starch in the film and/or foil produced is at least 500,000 g/mol.

12. The method of claim 1 wherein the weight-average molecular weight distribution $M_w2$ of the starch in the film and/or foil produced is at least 1,000,000 g/mol.

* * * * *